United States Patent [19]

McCormick

[11] 4,225,693
[45] Sep. 30, 1980

[54] PESTICIDE-POLYMER SYSTEMS PREPARED FROM VINYL MONOMERS

[76] Inventor: Charles L. McCormick, 2308 Clayton Pl., Hattiesburg, Miss. 39401

[21] Appl. No.: 932,724

[22] Filed: Aug. 10, 1978

[51] Int. Cl.$^2$ .............. A61K 31/78; C08F 20/22; C08F 20/34; C08F 22/38
[52] U.S. Cl. .................... 526/261; 424/19; 424/81; 526/243; 526/248; 526/258; 526/263; 526/274; 526/280; 526/284; 526/287; 526/288; 526/291; 526/292; 526/293; 526/296; 526/299; 526/304; 526/311; 526/312; 526/317; 526/320; 526/326; 526/328
[58] Field of Search ............. 424/81, 19; 526/240, 526/243, 245, 246, 248, 258, 261, 267, 274, 276, 277, 279, 280, 283, 286, 288, 292, 294, 298, 301, 309, 311, 312, 315, 316, 317, 320, 322, 326, 328, 263, 265, 284, 287, 291, 293, 296, 299, 304

[56] References Cited

U.S. PATENT DOCUMENTS

| | | | |
|---|---|---|---|
| 2,403,112 | 7/1946 | Muskat | 526/328 |
| 2,858,272 | 10/1958 | Cook | 526/328 |
| 3,116,271 | 12/1963 | Watt et al. | 526/328 |
| 3,476,722 | 11/1969 | Schlatzer | 526/328 |
| 3,772,258 | 11/1973 | Lachowicz | 526/328 |
| 4,062,855 | 12/1977 | Allan et al. | 424/78 |

*Primary Examiner*—Harry Wong, Jr.

[57] ABSTRACT

Controlled release pesticide-polymer systems are prepared by the polymerization of vinyl monomers containing pendant pesticides. The vinyl monomers are prepared by reacting an acrylic acid derivative with a pesticide or a pesticide derivative having an active hydrogen. The pesticide-polymer systems prepared from the pesticide vinyl monomers release the active pesticide material by hydrolysis or chemical depolymerization under conditions of use.

6 Claims, No Drawings

PESTICIDE-POLYMER SYSTEMS PREPARED FROM VINYL MONOMERS

BACKGROUND OF THE INVENTION

Numerous efforts have been made in the past to develope controlled release pesticides. One approach has been to coat particles of an insecticide with a polymeric coating, for examples, as described in U.S. Pat. No. 3,569,769 or U.S. Pat. No. 3,269,900. Another approach has been to chemically couple the pesticide directly to a natural polymeric substance, such as bark, as described in Canadian Pat. No. 863,310. Still another approach has been to use a bridging compound to chemically connect the pesticide to a natural polymeric substrate as described in Canadian Pat. No. 855,181. Pesticides also have been dissolved in waxes, incorporated in emulsions and combined with large amounts of inert carriers in efforts to obtain controlled release compositions.

None of the described approaches has been completely successful. Coating particles of a pesticide with a polymer film is a relatively expensive process; the use of natural polymer substrates, such as bark, can result in a product which is of non-uniform consistency from batch to batch and bulky to handle and transport, and the incorporation of a pesticide into emulsions, waxes and compositions including inert carriers can result in compositions which do not provide for an even controlled release of the active pesticide.

SUMMARY OF THE INVENTION

It is a general object of the present invention to disclose novel vinyl monomers containing pesticides and a method of polymerizing such monomers to obtain controlled release pesticide-polymer systems.

It is a further object to disclose novel pesticide-polymer systems which contain known pesticides and which will hydrolyze or depolymerize under conditions of use to yield an effective amount of the known pesticide.

It is a still further object to disclose novel, pesticide-polymer systems which are hydrolyzed or depolymerized over an extended period of time to release an effective amount of active pesticide at a controlled rate.

The novel pesticide-polymer systems of the present invention are prepared by the polymerization of vinyl monomers containing pendant pesticides. The pesticide vinyl monomers are in turn prepared by reacting an appropriate derivative of the acrylic acid with a pesticide or a pesticide derivative having an active hydrogen. The resulting polymer-pesticide systems release the pesticide under conditions of use in effective amounts at a predictable controlled rate.

DESCRIPTION OF THE PREFERRED EMBODIMENT

The novel pesticide-polymer systems of the present invention may be represented by the following formula:

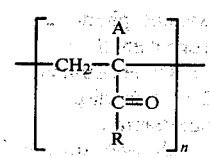

in which A is hydrogen, a lower alkyl of 1 to 5 carbon atoms such as methyl, ethyl, propyl, or isobutyl, a halide such as a chloride, bromide, iodide or fluoride, nitro or nitrile, R is a pesticide minus an active hydrogen or a pesticide derivative minus an active hydrogen, and n is 10 to 10 million.

The novel, pesticide-polymer systems are prepared by the polymerization of vinyl monomers containing the desired pesticide. The polymerization may be diagrammed as follows:

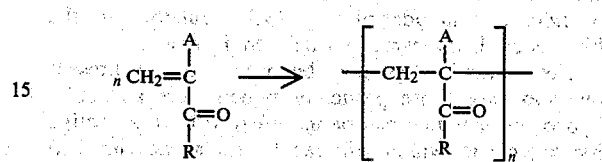

in which all symbols are as previously described.

In the preferred practice of the method of the invention, the vinyl monomers are polymerized in the absence of air at an elevated temperature. If desired, suitable polymerization catalysts, such as benzoyl peroxide, may be employed.

The novel vinyl monomer intermediates of the present invention may be prepared by reacting a pesticide or a pesticide derivative having an active hydrogen with a suitable acrylic acid derivative.

Pesticides or pesticide derivatives having a primary, or secondary amino group or a hydroxyl group may be reacted with an acryloyl chloride to obtain the desired monomer. The reaction may be diagrammed as follows:

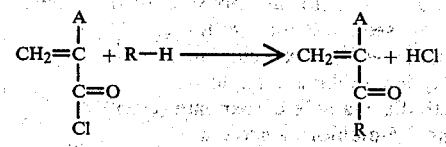

in which all symbols are as previously indicated.

When the active hydrogen of the pesticide is in a carboxylic acid group, the pesticide is first converted to the acid chloride and then reacted with an acrylamide. The reaction may be diagrammed as follows:

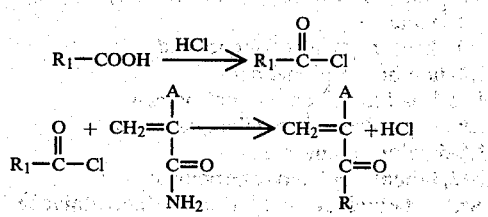

in which R is

$R_1$ is the non-carboxylic portion of a pesticide of the formula $R_1$—COOH and all other symbols are as previously indicated.

In some instances it may be desired to prepare monomers in which extenders have been inserted between the pesticide and the vinyl moiety of the monomer. In one such case, the pesticide in the form of an acid chloride is first reacted with aminoalkanol, such as aminoethanol, and the resulting pesticide derivative reacted with an acryloyl halide.

Further, examples of the preparation of the vinyl monomer can be found in the examples which are included in the specification which follows.

The term pesticide as employed herein is intended to include any active material used for biologic control of unwanted organisms including in particular insecticides, fungicides, herbicides, nemotocides and other biocides, and includes plant growth regulators and the like materials utilizable in a field environment.

The pesticides that may be used with the present invention are those pesticides which have an active hydrogen or which can be modified to have an active hydrogen and which will react with an acrylic acid derivative to form a suitable vinyl monomer.

Representative of the pesticides which may be employed as starting materials in the process are the following:

propen-1-ol-3
2-(ethylamine)-4-(isopropylamino)-6-(methylthio-s-triazine)3-amino-5-triazole
arsenic acid
methyl sulfanilyl carbamate
2-chloro-4-(ethylamino)-6-(isopropylamino)-s-triazine
(4-chloro-2-butynyl N-3(-chlorophenyl) carbamate
4-chloro-2-oxobenzothiazolin-3-ylacetic acid
N-butyl-N-ethyl-a,a,a-trifluoro-2,6-dinitro-p-toluidine
[S-(o,o-diisopropyl phosphorodithioate) ester of N-(2-mercaptoethyl) benzene sulfonamide]
3-isopropyl-1H-2,1,3-benzothiadiazin-4-(3H)-one 2,2-dioxide(benzamidooxy) Acetic Acid
methyl-5-(2,4-dichlorophenoxy)-2-nitrobenzoate
5-bromo-3-sec-butyl-6-methyluracil
3,5-dibromo-4-hydroxybenzonitrile
hydroxydimethylarsine oxide
D-N-ethyllacetamide carbanilate (ester)
3-amino-2,5-dichlorobenzoic acid
3-(4-bromo-3-chlorophenyl)-1-methoxy-1-methylurea
methyl-2-chloro-9-hydroxyfluorene-9-carboxylate
3-[p-(p-chlorophenoxy)phenyl]-1,1-dimethylurea
isopropyl-m-chlorocarbanilate
2[[4-chloro-6-(ethylamino)-s-triazin-2-yl]Amino]-2-methylpropionitrile
2-chloro-4-(cyclopropylamino)-6-(isopropylamino)-s-triazine
(2,4-dichlorophenoxy)acetic acid
2,2-dichloropropionic acid
4-(2,4-dichlorophenoxy)butyric acid
ethyl m-hydroxycarbanilate carbanilate
3,6-dichloro-o-anisic acid
2-(2,4-dichlorophenoxy)propionic acid
$N^4,N^4$-diethyl-a,a,a-trifluoro-3,5-dinitrotoluene-2,4-diamine
2-sec-butyl-4,6-dinitrophenol 2,4-bis(isopropylamino)-6-(ethylthio)-s-triazine
3-(3,4-dichlorophenyl)-1,1-dimethylurea
7-oxabicyclo [2,2,1]heptane-2,3-dicarboxylic acid
2-chloroethylphosphonic acid
(2,3,6-trichlorophenyl)acetic acid
1,1-dimethyl-3-phenylurea mono(trichloroacetate)
1,1-dimethyl-3-(a,a,a-trifluoro-m-tolyl)urea
n-butyl-9-hydroxyfluorene-(9)-carboxylate
N-(phosphonomethyl) glycine
N,N-bis(phosphonomethyl) glycine
2-methoxy-4-ethylamino-6-sec-butylamino-s-triazine 4-hydroxy-3,5-diiodobenzonitrile
3-(m-hydroxyphenyl)-1,1-dimethylurea
3-(3,4-dichlorophenyl)-1-methoxy-1-methylurea methanearsonic acid
N-[3-[(1,1,1-trifluoromethylsulfonyl)Amino]-4-methylphenyl]acetamide
1,1,1-trifluoro-N-[2-methyl-4-(phenylsulfonyl)phenyl]-methanesulfonamide
2-methyl-4-chlorophenoxyacetic acid
4[(4-chloro-o-tolyl)oxy]butyric acid
2-[(4-chloro-o-tolyl)oxy]propionic acid
4-amino-6-tert-butyl-3-(methylthio)-as-triazin-5(4H)one
1,2-dihydro 3,6-pyridazinedione
3-(p-chlorophenyl)-1,1-dimethylurea
1-naphthalene acetic acid
N-1-naphthylphthalamic acid
6-tert-butyl-3-isopropylisoxazolo-[5,4-d]pyrimidin-4(5H)-one
3-(hexahydro-4,7-methanoindan-5-yl)-1,1-dimethylurea
4-chloro-5-(methylamino)-2-(a,a,a-trifluoro-m-tolyl)-3-(21t)-pyridazinone
3,5-dinitro $N^4,N^4$-dipropylsulfanilamide
methyl m-hydroxycarbanilate m-methylcarbanilate
4-amino-3,5-6-trichloropicolinic acid
p-chlorophenyl N-methylcarbamate
2,4-bis(isopropylamino)-6-methoxy-s-triazine
2,4-bis(isopropylamino)-6-(methylthio)-s-triazine
N,-(1,1-dimethylpropynyl)-3,5-dichlorobenzamide
3',4'-dichloropropionanilide
2-chloro-4,6-bis(isopropylamino)-s-triazine
isopropyl carbanilate
5-amino-4-chloro-2-phenyl-3(2H)-pyridazinone
1-(2-methylcyclohexyl)3-phenylurea
2-(2,4,5-trichlorophenoxy)propionic
2-chloro-4,6-bis(ethylamino)-s-triazine
(2,4,5-trichlorophenoxy)acetic acid
2,3,6-trichlorobenzoic acid
trichloroacetic acid
3-tert-butyl-5-chloro-6-methyluracil
2-chloro-4-ethylamino-6-tert-butylamino-s-triazine
2,6-di-tert-butyl-p-tolyl methylcarbamate
2-methylthio-4-ethylamino-6-tert-butylamino-s-triazine
2,3,5-triiodobenzoic acid
-s-(2,3,3,-trichloroallyl)diisopropylthiocarbamate
-s-propyl dipropylthiocarbamate
acroeline phenylhydrazone
2-amino-3-chloro-1,4-naphthoquinone
4-amino pteroylglutamic acid
p-tert-amyl phenol
2-(3'-pyridyl) piperidine
2,4-dichloro-6-(2-chloroanil-o)-1,3,5 triazine
1-decanol
1-(1-naphthyl)-2-thiourea
2-iodobenzanilide
1,4-benzoquinone-1-benzoyl-hydrozone-4-oxime
4-chloro-3,5-xylenol
n-butyl-p-hydroxybenzoate
benzoyl-8-hydroxyquinoline salicylate
3-(sec-butyl) phenyl-N-methylcarbamate
3,5-dibromo-4-hydroxybenzaldehyde O-(2,4-dinitrophenyl) oxime
2-bromo-4'-hydroxyacetophenone
isopropyl 4,4'-dibromobenzilate
3,5-dibromo-4-hydroxybenzonitrile
2-ethyl-2-butyl-1,3-propanediol
1-naphthyl methylcarbamate
2,3-dihydro-2,2-dimethyl-benzofuran-7-yl-methylcarbamate chlorobenzenesulfonamide
monochloroacetic acid
cis-3-chloroacrylic acid
3-amino-2,5-dichlorobenzoic acid
2,2'-thiobis(4-chloro-6-methylphenol)
3-(4-bromo-3-chlorophenyl)-1-methoxy-1-methylurea
1-methyl-2-propynyl-m-chlorocarbanilate
ethyl 4,4'-dichlorobenzilate
4-chloro-m-cresol
4-chloro-2-cyclopentyl phenol
5-chloro-4-methyl-2-propionamidothiazole
2,2,3-trichloropropionic acid
isopropyl 4,4'-dichlorobenzilate
6-chloro thymol
3,5-dichloro-4-hydroxybenzonitrile
o-benzyl-p-chlorophenol
3-(a-acetonyl-4-chlorobenzyl)-4-hydroxycoumarin
2-(3-chlorophenoxy)a-propionamide
2-(3-chlorophenoxy) propionic acid
2-chlorophenyl-N-methylcarbamate
2-(4-chlorophenoxy) propionic acid
o-cresol
m-cresol
p-cresol
a-cyano-B-(2,4-dichloro)-cinnamie acid
N-cyclohexyl 2,5-dimethyl-3-furamide
3-(4-cyclopropylphenyl)-1,1-dimethylurea
3-cyclo-octyl-1,1-dimethylurea
o,o-dimethyl o-p-sulfamoylphenyl phosophorothioate
2,2-dichloropropionic acid
1,3-bis(1-hydroxy-2,2,2-trichloroethyl)urea
3,6-dichloro-2-methoxybenzoic acid
2,2-methylenebis (4-chlorophenol)
2,4-dichloro phenoxy acetamide
2-(3,4-dichlorophenoxy)propionic acid
1,1-bis(p-chlorophenyl)-2,2,2-trichlouethanol
O,O-dimethyl S-(N-methyl-carbamoylmethyl) phosphorodithioate
4,6-dinitro-o-cresol
2,4-dinitro-6-cyclohexyl phenol
2,4-dinitrophenol
2,5-dichloro-3-nitrobenzoic acid
2,4 dinitro-6-sec-butylphenol
2,4-dinitro-6-tert-butylphenol
1,1-bis(p-chlorophenyl)ethyl carbinol fluoroacetamide
fluoroacetanilide
3-hydroxy-5-methylisoxazole
2-hydroxymethyl-4-chlorophenyloxyacetic acid
3-inddylpropionic acid
4-chloro-2-methylphenoxy acetic acid
4-(4-chloro-2-methylphenoxy)butyric acid
3-methyl-2,4-dinitro-6-tertbutyl phenol
bishydroxy coumarin
methyl p-hydroxybenzoate
cyclopentane carboxylic acid
B-naphthol
a,a-bis (p-chlorophenyl)-3-pyridine-methanol
nonylic acid
2,3,4,5,6-pentachlorobenzylalcohol
pentachlorophenol
2-phenylcyclohexanol
2-hydroxy diphenyl
N-phenyl-N'-3-thiolane-1-dioxide hydrazide
4-amino-3,5,6-trichloropicdinic acid
2-hydroxybenzhydroxamic acid
2,4 hexadienoic acid
1,1'-methylenedi-2-naphthol
2,3,6-trichlorobenzoic acid
3,4',5-tribromosahcylanilide
3-trifluoromethyl-4-nitrophenol
2,3,5-triiodobenzoic acid
3,5,6-trichloro-2-methoxybenzoic acid
2,4,6-trichlorophenol
2,4,5-trichlorophenol
2-(hydroxymethyl)-2-nitro-1,3-propanediol
2,3,6-trichlorobenzyloxypropanol
10-undecenoic acid
2,4-dimethyl phenol Obviously the foregoing list is not complete, for as previously indicated, almost any pesticide having an active hydrogen, or which can be modified to have an active hydrogen, and which does not contain other groups that will interfere with the monomer forming reaction or the polymerization reaction may be employed.

The pesticides which are especially preferred are: trichloroacetic acid, 2,4-dichlorophenoxyacetic acid (2,4-D), and the relatively new pesticide 4-amino-6-tert-butyl-3-(methylthio)-as-triazine-5(4H) one which is available under the name metribuzin.

Representative of the acrylic acid derivatives that can be used in the preparation of the vinyl monomer intermediates are acrylic acid, acryloyl chloride, acryloyl bromide, acrylamide and substituted derivatives thereof.

In a preferred embodiment, the preparation of the vinyl monomer is conducted in a mutual solvent for the reactants, e.g., tetrahydrofuran, and the reaction mixture is maintained at a temperature of about 20°-60° C. for about 4 to about 24 hours or until the reaction is complete as indicated by analysis of the reaction mixture.

The preparation of the pesticide-polymer system is generally conducted by heating the monomer in the absence of air with or without a polymerization catalyst in a suitable polymerization vessel. In a preferred embodiment, the monomer is charged into a polymerization vessel which is purged with nitrogen, the vessel is sealed, and heated in an oil bath at a temperature of about 45°-150° C. until the reaction is complete. Polymerization can be confirmed by I.R. and N.M.R. data. When polymerization is complete, the reaction mixture is preferably extracted with a solvent such as heptane and the pesticide-polymer system precipitated and dried. Other conventional methods for separating the desired polymer-pesticides systems from the reaction mixture also can be utilized.

The resulting pesticide-polymer systems can, if desired, be powdered or granulated and/or bonded with other active or inactive ingredients to form suitable compositions for use under field conditions which will depolymerize to yield an effective amount of the pesticide.

The pesticide-polymer systems of the present invention can be tailored to provide and release an effective amount of the pesticide under almost any type of conditions by a proper selection of ingredients. In addition, they are of readily determinable molecular weight and structure, making it possible to determine in advance the precise amount of system needed to controllably release an effective amount of the pesticide under a given set of field use conditions.

Although tetrahydrofuran is the preferred solvent, other suitable solvents can be used, such as dimethylacetamide, N,N-dimethylformamide, and dimethylsulfoxide.

The following examples are presented to illustrate the practice of the invention.

EXAMPLE I (Part A)

Preparation of 2,4-D Vinyl Monomer Containing an Amide Linkage

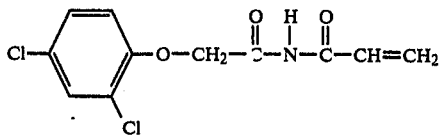

A 500 ml three neck flask, equipped with mechanical stirrer, thermometers, and condenser, was charged with 200 parts of double distilled THF, 7.2 parts of acrylamide and 15 parts of trimethylpyridine. The contents of the flask were stirred and heated about 30° C.–35° C. for ½ hour. To the reaction mixture was added a mixture consisting of 50 parts of tetrahydrofuran (THF) and 25 parts of the acid chloride of 2,4-D herbicide within a period of ½ hour. Upon the completion of acid chloride addition, the reaction was continued at a temperature of 30° C.–35° C. for an additional 8 hours. The contents of the vessel were cooled to 25° C. and filtered under suction. The filtrate was stripped off under vacuum and the residue extracted from heptane to yield the desired monomer (m.p. 120° C.). The monomer was washed in heptane twice, filtered and dried under vacuum. The IR and NMR date complied with the structure of compound.

(Part B)

Preparation of 2,4-D Polymer Containing an Amide Linkage

Into each of 4 polymerizing tubes was added 2 grams of the monomer described in Part A followed with the addition of 0.001 grams of benzoyl peroxide, 0.003 grams of benzoyl peroxide, and 0.006 grams of benzoyl peroxide to the first three tubes respectively; no peroxide was added to the fourth tube. Then 5 ml of double distilled THF was added to each tube. The tubes were purged with $N_2$ for 5 minutes. Each tube was sealed, and all four tubes were placed in an oil bath of constant temperature of 45° C. for a period of 24 hours. The tubes were then cooled to 25° C., the seals were broken, the contents precipitated with heptane, and the polymers dried under vacuum. The formation of polymers was confirmed by the absence of IR, UV, absorption peaks at the region of 3035 cm$^{-1}$, 1645 cm$^{-1}$ and 885 cm$^{-1}$ as well as with the absence of NMR complex peaks at regions of 5 § to 6 §.

EXAMPLE II (Part A)

Preparation of 2,4-D Vinyl Monomer Containing an Ester Linkage with Ethylene Extender

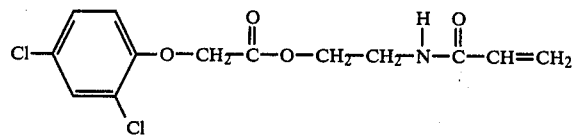

An apparatus similar to that described in Part A of Example I was charged with 200 parts of double distilled THF, 7 parts of ethanol amine, and 4 parts of sodium. The contents of the vessel were stirred and heated at about 50° C. for a period of 3 hours. The mixture was then cooled to 15° C. while stirring; and a mixture consisting of 25 parts of acid chloride of 2,4-D, and 50 parts of THF added within a period of 2 hours while maintaining the temperature of the reaction during the addition at 15°–20° C. Upon the completion of addition, the reaction was allowed to continue for an additional 9 hours at 25° C. The progress of the reaction was maintained by IR. Upon the complete formation of the ester linkages, a second mixture consisting of 25 parts of THF and 10.0 parts of acrylchloride was added within an hour at temperature of 15°–20° C. When the addition was completed, the reaction was allowed to run for an additional 8 hours at 25° C. The reaction progress was maintained and controlled by the absence of IR absorption peak of amine, the presence of IR absorption for amide peak, and IR absorption peaks for the vinyl group. Upon the completion of the reaction, the contents of the flask were filtered under suction. The filtrate was stripped under vacuum; while the residue was extracted by heptane, resulting in a yield of 28 parts of liquid monomer. The monomer was washed with THF and precipitated with heptane twice and dried under vacuum over sodium sulfate.

(Part B)

Preparation of 2,4-D Polymers Containing an Ester Linkage and Ethylene Extender

A polymerizing tube was charged with 2 parts of the 2,4-D vinyl monomer of Part A. The tube was purged with nitrogen for 5 minutes, sealed, and then placed in an oil bath of constant temperature of 135° C. for a period of 24 hours. At the end of the reaction, the tube was cooled, and the content was extracted from heptane, resulting in a yield of 1.6 parts. Both IR and NMR data showed the formation of the desired polymer.

EXAMPLE III (Part A)

Preparation of Trichloracetic Acid (TCA) Vinyl Monomer Containing an Amide Linkage

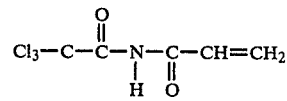

To an apparatus similar to that of Part A of Example I was added 100 parts double distilled THF, 8.0 parts of acrylamide, and 15 parts of trimethylpyridine. The mixture was stirred and heated at 35° C. for 1 hour. A mixture consisting of 19.0 parts of acid chloride of TCA and 50 parts of THF was added to the apparatus within a period of 3 hours, maintaining the temperature of the reaction at 25°–30° C. Upon the completion of the addition, the reaction was allowed to proceed for an additional 8 hours at temperature of 30°–35° C. The formation of vinyl monomer was maintained by IR. The complete absence of amine peaks and the presence of an amide peak followed by the appearance of a vinyl group in the appropriate IR region were taken as the end of reaction. The contents of the batch were cooled and filtered under suction. The filtrate was stripped under vacuum and the residue was extracted from heptane resulting in a yield of 21 grams of the desired monomer.

(Part B)

Preparation of TCA Polymer Containing an Amide Linkage

Into a polymerizing tube was added 3 parts of the TCA monomer of Part A. The tube was purged with nitrogen for 5 minutes, sealed, and placed in an oil bath of constant temperature of 135° C. for a period of 24 hours. At the end of the reaction, the mass was cooled, extracted with ethanol and the polymer precipitated with heptane to yield 2.6 parts of the desired polymer.

EXAMPLE IV

(Part A)

Preparation of TCA Vinyl Monomer Containing an Ester Linkage with Ethylene Extender Into an apparatus similar to that employed in Part A of Example I was placed 200 parts of double distilled THF, 8.0 parts of ethanolamine and 4 parts of sodium. The reaction was stirred and heated to 30°–40° C. for 5 hours. The reaction was cooled to 20° C. A mixture consisting of 19 parts of the acid chloride of TCA and 50 parts of THF was then added within a period of 2 hours while maintaining the reaction temperature at about 20°–24° C. during the entire addition. Upon the completion of addition, the reaction was allowed to run for an additional 8 hours at a temperature of 25° C. The progress of the reaction as it was evidenced by the rate of formation of ester was checked by IR.

A second mixture consisting of 10.0 parts of acryloyl chloride and 40 parts of THF was added to the reaction within 2 hours while maintaining the reaction temperature at 25° C. The entire reaction mass was allowed to run for an additional 9 hours. The formation of the vinyl group was controlled by IR spectrophotometer. Upon the complete formation of vinyl group and the disappearance of amino absorption, the reaction was stopped. The mass was filtered under suction, the filtrate stripped under vacuum. The residue was extracted with heptane, resulting a yield of 22 grams of the desired monomer.

(Part B)

Preparation of TCA Polymer Containing an Ester Linkage

Into each of 4 polymerizing tubes was added 1.1 grams of the monomer described in Part B of this Example. Peroxide catalyst was added to three of the tubes. The tubes were then purged with nitrogen for 5 minutes, sealed, and placed in an oil bath at a constant temperature of 103° C. for a period of 24 hours. The tubes were shaken occasionally during the course of the reaction. The tubes were cooled, the polymers extracted by THF and precipitated with heptane. The IR and NMR data confirmed the structure. The compounds had a molecular weight (mn) of 1,108,000 as determined by use of a membrane osmometer.

| Tubes | Parts Peroxide | Mn | Parts Yield | Parts Monomer |
|---|---|---|---|---|
| 1 | 0.0076 | 168,000 | 1 | 1.1 |
| 2 | 0.0132 | 93,000 | 0.99 | 1.14 |
| 3 | 0.0018 | 182,000 | 0.95 | 1.12 |
| 4 | 0 | 458,000 | 0.98 | 1.00 |

EXAMPLE V

(Part A)

Preparation of 2,2-Dichloropropionic Acid—(DALAPON) Vinyl Monomer Containing Anhydride Linkage Into an apparatus similar to that of Example I was added 100 parts of double distilled THF, 3.5 parts of anhydrous potassium carbonate and 7.2 parts of 2,2-dichloropropionic acid (Dalapon). The mixture was stirred and refluxed for two hours. The vessel was cooled to 35° C. and a mixture consisting of 11.0 parts of methacryl chloride and 40 parts of THF within a period of ½ hour. Upon completion of the addition, the mixture was allowed to run an additional 15 hours as required for complete substitution of vinyl group as evidenced by IR. The mixture was filtered under suction. The filtrate was stripped under vacuum and the residue was extracted from heptane, resulting a yield of 5.5 grams of the desired monomer.

Analysis for $C_7H_8Cl_2O_3$

| Theory | C% | 39.81 | Found | 39.29 |
|---|---|---|---|---|
| | H% | 3.82 | | 3.38 |
| | Cl% | 33.65 | | 33.76 |

(Part B)

Preparation of 2,2-Dichloropropionic Acid Polymer Containing an Anhydride Linkage Into a polymerizing tube charged with 1.0 parts of the monomer prepared in Part A was added 5 parts of double distilled THF. The mixture was purged with nitrogen for 5 minutes. The tube was sealed and placed in an oil bath of constant temperature of 130° C. for a period of 24 hours. The tube was cooled and the polymer was filtered. The solid crystals obtained were washed twice with THF. The IR data indicated the presence of the desired polymer.

EXAMPLE VI

(Part A)

Preparation of a Vinyl Monomer of 2,2-Dichloropropionic Acid Containing an Ester Linkage and an Ethylene Extender Into an apparatus similar to that of Example I, was added 200 parts of double distilled THF, 4.0 parts of sodium and 8.0 parts of ethanolamine. The mixture was stirred and heated at 50° C. for a period of 3 hours. The mixture was then cooled to 20° C. and a mixture consisting of 160 parts of the acid chloride of 2,2-dichloropropionic acid and 50 parts of THF was added within a period of 2 hours maintaining the temperature during addition at 20° C. Upon the completion of addition, the reaction was allowed to run an additional 10.0 hours at the designated temperature. Upon completion of the formation of the ester linkage as evidenced by IR data, a second mixture consisting of 10 parts of acryl chloride and 40 parts of THF were added within 2 hours at 20° C. Upon the completion of addition, the mixture was allowed to run an additional 9 hours in order to substitute the vinyl group on the compound. At the end of the reaction, the contents were filtered under suction, the filtrate was stripped under vacuum, and the residue was extracted from heptane, resulting a yield of 21 parts of the desired monomer. The structure of monomer complied with both IR and NMR data.

(Part B)

Preparation of 2.2-Dichloropropionic Acid Polymer Containing an Ester Linkage and an Ethylene Extender A polymerizing tube charged with 2 parts of the monomer of Part A was purged with nitrogen for 5.0 minutes, sealed, and placed in an oil bath of constant temperature of 135° C. for a period of 24 hours. At the end of reaction, the tube was cooled, the residue was extracted from THF and precipitated from heptane to yield the desired polymer. The polymer complied with both IR and NMR data.

EXAMPLE VII (Part A)

Preparation of Metribuzin Vinyl Monomer Containing an Amide Linkage

Into an apparatus similar to that described in Example I charged with 100 parts of double distilled THF was added 10.0 parts of metribuzin. The mixture was stirred for 1 hour at 30° C. A mixture consisting of 6 parts of acryl chloride and 25 parts of THF was then added within a period of ½ hour while maintaining the temperature at 30° C. during the addition. The reaction was allowed to run for a period of 24 hours while the reactor was purged with a gentle stream of nitrogen during the entire reaction. At the end of reaction, 50% of THF was stripped off under vacuum. The product was precipitated from the remaining THF by heptane, resulting a yield of 11.0 parts of the desired monomer m.p. 160° C. (die).

Analysis of $C_{11}H_{16}O_2N_4S$

| Theory | C% | 49.25 | Found | 48.80 |
|---|---|---|---|---|
| | H% | 6.01 | | 6.22 |
| | N% | 20.85 | | 20.12 |
| | S% | | | 10.97 |

The NMR analysis of described compound is tabulated below:

| Designated Protons | # of Protons | s value | Solvents | Ref. |
|---|---|---|---|---|
| a | 9 | 1.35 (s) | d$_6$auton | TMS |
| b | 3 | 2.55 (s) | " | " |
| c | 1 | 9.9 (s) | " | " |
| d & e | 3 | 5.9–7.5 | " | " |

(Part B)

Preparation of Metribuzin Polymer Containing an Amide Linkage

Into each of four polymerizing tubes was added one part of metribuzin monomers followed with the addition of 0.0171, 0.0102 and 0.0366 parts of benzoyl peroxide to the first three tubes respectively; whereas, no peroxide was added to the fourth tube. Each tube was purged with nitrogen for 5 minutes, sealed, and all were placed in an oil bath of constant temperature of 135°±5° C. for 72 hours. At the end of the reaction, they were cooled, and each sample was extracted from THF and precipitated with heptane. The results are tabulated and summarized in the following tables:

TABLE A

| # Tubes | Parts Monomer | Peroxide Part | Mn | Yield Parts | By Time |
|---|---|---|---|---|---|
| 1 | 1 | 0.0171 | 80,800 | 0.90 | 72 |
| 2 | 1 | 0.0101 | 270,000 | 0.94 | 72 |
| 3 | 1 | 0.0366 | 38,600 | 0.87 | 72 |
| 4 | 1 | none | 317,000 | 0.72 | 72 |

TABLE B

Analysis of $C_{11}H_{16}O_2N_4S$ polymer Mn = 317,000

| Theory | C% | 49.25 | Found | 48.60 |
|---|---|---|---|---|
| | H% | 6.01 | | 6.30 |
| | N% | 20.85 | | 19.92 |
| | S% | 11.85 | | 10.91 |

EXAMPLE VIII (Part A)

Preparation of Metribuzin Vinyl Polymer Containing an Urea Linkage

Into an apparatus similar to that of Example I was added 200 parts of THF, 2.0 parts of sodium and 8.0 parts of ethanolamine. The mixture was stirred and heated at 50° C. and a mixture consisting of 10.0 parts of acryl chloride and 50 parts of THF added within a period of one hour whiling maintaining the temperature of the reaction at 20° C. during the addition. Upon the completion of the addition, the reaction was allowed to run for an additional 8 hours, until the formation of ester was completed as evidenced by IR data. Upon the formation of the ester, 1.0 parts of tributyl amine was added, followed with the slow addition of 24 parts of metribuzin isocyanate. Upon the completion of the addition of the metribuzin isocynate, the reaction was allowed to run a total of 24 hours or until the complete conversion of amine into amide was evidenced by both IR and NMR data. At the end of the reaction, the contents were filtered under the suction, the filtrate was stripped under vacuum, and the residue was extracted from heptane to yield 30 parts of the desired polymer.

(Part B)

Preparation of Metribuzin Polymer Containing an Urea Linkage and an Ethylene Extender Into a polymerizing tube was added 1.5 parts of the monomer of Part A and 0.0082 parts of benzoyl peroxide. The tube was purged with nitrogen for 5 minutes; it was then sealed and placed in an oil bath of constant temperature 135° C. for a period of 24 hours. At the end of the reaction, the tube was cooled and the product was extracted by THF and precipitated with heptane to yield 1.3 parts of the polymer as a thick gummy material. The IR and the NMR data showed that the monomer had been converted into the desired monomer.

EXAMPLE IX (Part A)

Preparation of 2-sec-butyl-4,6-dinitrophenol (DINITROL) Vinyl Monomer Containing an Ester Linkage Into an apparatus similar to that of Example I was added 155 parts of THF, 12.0 parts of 2-sec-butyl-4,6-dinitrophenol and 7 parts anhydrous $K_2CO_3$. The reaction was stirred and refluxed for 3 hours. The vessel was cooled to 30° C. and a mixture consisting of 6 parts of acryl chloride and 20 parts of THF added within a period of ½ hour while maintaining the temperature of reaction during the addition at 20° C.-25° C. Upon the completion of the addition, the reaction was allowed to run for an additional 10 hours. The mass was filtered, and the filtrate stripped under vacuum. The residue was extracted from heptane, resulting in a yield of 10 parts of the monomer as nice yellow crystals (m.p. 160° C.).

The analysis of $C_{13}H_{14}O_6N_2$

| Theory: | C% | 53.06 | Found: | 53.23 |
|---|---|---|---|---|
| | H% | 4.76 | | 3.98 |
| | N% | 9.52 | | 9.65 | stant temperature of 175° C. for a period of 48 hours. At the end of the reaction, the vessel was cooled and the mass extracted from THF and precipitated with heptane to yield 1.7 parts of the desired polymer (m.p. 200° C.). The polymer structure complied with both IR and NMR data.

Additional acrylic monomers containing pendant herbicides of metribuzin, trichloroacetic acid, and 2,4-dichlorophenoxyacetic acid were synthesized and polymerized.

Experimental data including polymerization conditions, percent yield, weight, percent herbicide, and number average molecular weight are given for the additional polymers in Table I.

TABLE I.

Physical Date for the Polymerization of Acrylic Herbicide Monomers

| Sample Number | Monomer Structure | Monomer conc (Moles × $10^{-3}$) | Initiator conc. (Moles × $10^{-5}$) | Solvent | T(°C. ± 5) | Rxn Time (hrs) | % Yield | Mn. | % by wt. Herbicide |
|---|---|---|---|---|---|---|---|---|---|
| 1 | $R_1COCH=CH_2$ | 3.7 | 7.07 | — | 135 | 72 | 86 | 80,800 | 80 |
| 2 | $R_1COCH=CH_2$ | 3.7 | 4.22 | — | 135 | 72 | 94 | 270,000 | 80 |
| 3 | $R_1COCH=CH_2$ | 3.7 | 15.1 | — | 135 | 72 | 87 | 38,600 | 80 |
| 4 | $R_1COCH=CH_2$ | 3.7 | 0 | — | 135 | 72 | 69 | 317,000 | 80 |
| 5 | $R_1COCH=CH_2$ | 3.4 | 0 | THF | 50 | 44 | 58 | 733,000 | 80 |
| 6 | $R_1COCH=CH_2$ | 4.8 | 1.69 | THF | 50 | 44 | 42 | 504,000 | 80 |
| 7 | $R_1COCH=CH_2$ | 4.0 | 7.48 | THF | 50 | 44 | 50 | 311,000 | 80 |
| 8 | $R_1COCH=CH_2$ | 3.9 | 2.93 | THF | 50 | 44 | 52 | 369,000 | 80 |
| 9 | $R_1COCH=CH_2$ | 6.0 | 8.26 | — | 150 | 30 | 75 | 202,000 | 80 |
| 10 | $R_1COCH=CH_2$ | 6.0 | 0 | — | 150 | 48 | 60 | 90,700 | 80 |
| 11 | $R_1COCH=CH_2$ | 6.0 | 0 | — | 30 | 100 | 69 | 968,000 | 80 |
| 12 | $R_1COC(CH_3)=CH_2$ | 4.9 | 8.26 | THF | 65 | 15 | 96 | 570,000 | 76 |
| 13 | $R_1COC(CH_3)=CH_2$ | 3.5 | 8.36 | — | 160 | 44 | 15 | 52,200 | 76 |
| 14 | $R_1COC(CH_3)=CH_2$ | 3.5 | 0 | — | 160 | 44 | 72 | 35,200 | 76 |
| 15 | $R_1COC(CH_3)=CH_2$ | 3.5 | 6.20 | — | 160 | 44 | 68 | 31,400 | 76 |
| 16 | $R_1COC(CH_3)=CH_2$ | 3.5 | 4.13 | — | 160 | 44 | 73 | 181,000 | 76 |
| 17 | $R_1COC(CH_3)=CH_2$ | 3.7 | 4.13 | THF | 45 | 44 | 94 | 150,000 | 76 |
| 18 | $R_1COC(CH_3)=CH_2$ | 3.6 | 1.98 | THF | 45 | 44 | 96 | $10^6$ | 76 |
| 19 | $R_1COC(CH_3)=CH_2$ | 3.8 | 5.04 | THF | 45 | 44 | 93 | 99,000 | 76 |
| 20 | $R_1COC(CH_3)=CH_2$ | 3.4 | 0 | THF | 45 | 44 | 90 | 118,500 | 76 |
| 21 | $R_2X_4COCH=CH_2$ | 17.0 | 0 | THF | 35 | 100 | 85 | 847,000 | 69 |
| 22 | $R_2X_4COCH=CH_2$ | 33.0 | 0 | THF | 35 | 100 | 82 | 785,000 | 62 |
| 23 | $R_2X_4COCH=CH_2$ | 15.0 | | THF | 25 | 100 | 90 | 645,000 | 62 |
| 24 | $R_2X_4COCH=CH_2$ | 27.0 | 0 | THF | 35 | 100 | 90 | $10^6$ | 62 |
| 25 | $R_2X_4COCH=CH_2$ | 4.1 | 3.14 | — | 115 | 24 | 93 | 93,000 | 62 |
| 26 | $R_2X_4COCH=CH_2$ | 4.3 | 5.45 | — | 115 | 24 | 87 | 168,000 | 62 |
| 27 | $R_2X_4COCH=CH_2$ | 4.3 | 0.74 | — | 115 | 24 | 84 | 182,000 | 62 |
| 28 | $R_2X_4COCH=CH_2$ | 3.8 | 0 | — | 115 | 24 | 90 | 458,000 | 62 |
| 29 | $R_2X_4COCH=CH_2$ | 4.2 | 3.47 | — | 135 | 24 | 87 | 309,000 | 60 |
| 30 | $R_2X_4COCH=CH_2$ | 4.2 | 5.58 | — | 135 | 24 | 85 | $10^6$ | 60 |
| 31 | $R_2X_4COCH=CH_2$ | 4.2 | 1.49 | — | 135 | 24 | 87 | 294,000 | 60 |
| 32 | $R_2X_4COCH=CH_2$ | 4.2 | 0 | — | 135 | 24 | 93 | 248,000 | 60 |

Symbols and Abbreviations for Table I

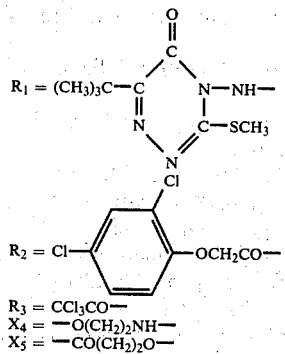

$R_1 = $ (metribuzin-derived structure)

$R_2 = $ (2,4-dichlorophenoxyacetyl structure)

$R_3 = CCl_3CO-$
$X_4 = -O(CH_2)_2NH-$
$X_5 = -CO(CH_2)_2O-$

(Part B)

Preparation of a 2-sec-butyl-4,6-dinitrophenol Polymer Containing an Ester Linkage Into a polymerizing tube was placed 2 parts of the monomer of Part A. The tube was purged with nitrogen for 5 minutes, sealed, and placed in an oil bath of con- Polymers from Metribuzin-Containing Monomers Metribuzin-containing monomers, 1-20 (Table I), were prepared by reacting equimolar amount of acryloyl chloride or methacryloyl chloride with metribuzin in terahydrofuran. Polymerizations were conducted in bulk and in solution using benzoyl peroxide or simple thermal initiation. Molecular weights as determined by membrane osometry varied with initiator concentration, reaction time, and temperature. The resulting polymers had number average molecular weights ranging from 40,000 to 1,000,000.

Monomers 29–32 (Table I) were prepared by reacting 2-hydroxyethyl acrylate with 4-isocyanato-6-tert-butyl-3-(methylthio-as-triazin-5(4H)one. Bulk polymerization with benzoyl peroxide initiators at 135° C. for 24 hours yielded ethanol-soluble polymers with number average molecular weights up to 1,000,000.

Polymers of N-(Trichloroacetyl) Acrylamide

Monomers 22–28 (Table I) were synthesized by reacting the 2-amino-ethylester of trichloroacetic acid with an equimolar amount of acryloyl chloride. The monomers are polymerized in tetrahydrofuran and in bulk using benzoyl peroxide initiation. The ethanol-soluble polymers were determined to have number average molecular weights between 93,000 and 1,000,000.

Polymer of N-Acryloyl-O-(2,4-Dichlorophenoxyacetyl)-Ethanolamine

Monomer 21 (Table I) was synthesized by reacting the 2-amino ethylester of 2,4-chichlorophenoxyacetic acid with acryloyl chloride. The resulting monomer was polymerized in tetrahydrofuran using thermal initiaiton yielding a polymer of Mn=847,000 as determined by membrane osmometry.

Polymers of the Mixed Anhydride of Acrylic Acid and 2,4-Dichlorophenoxyacetic Acid The mixed anhydride monomer of 2,4-chlorophenoxyacetic acid and acrylic acid was prepared by reacting acryloylchloride with 2,4-dichlorophenoxyacetic acid. The monomer was polymerized in solution (THF) and bulk using benzoyl peroxide initiator. The resulting polymers were insoluble in all organic solvents tested. The anhydride linkages, however, rapidly hydrolyzed to yield ethanol soluble copolymers. Due to the insolubility, characterization of the unhydrolyzed copolymers was limited to infrared analysis which confirmed the existence of the anhydride absorbance in the $1830^{-1}$ region.

The polymers in Table I exhibit controlled release profiles. 12, for example, exhibits a constant rate of releate over a twenty-four hour period in distilled water. This behavior is probably a result of the change in the solubility parameter of the copolymer surface with hydrolysis. Although the surface concentrations of labile bonds are reduced with time, the acrylic acid groups which form increase hydrophilicity and thus penetration of water to the susceptible bonds on the interior of the particles. Additionally, further hydrolysis may be catalyzed by the newly formed carboxylic acid groups.

It will be apparent to those skilled in the art that the controlled release polymer pesticide systems of the present system which can be tailored to release effective amounts of the pesticide over a substantial period of time provide several substantial advantages over the use of the pesticides per se. For example, such controlled release pesticides can reduce environmental pollution in non-target areas by reducing pesticide mobility and provide economic benefits as they also require fewer applications during the growing season.

It will be readily apparent to those skilled in the art that a number of modifications and changes can be made without departing from the spirit and scope of the present invention. Therefore, it is not intended that the invention be limited by the illustrative examples but only by the claims which follow.

I claim:

1. A pesticide-polymer which provides for the controlled release of the pesticide under conditions of use represented by the following formula:

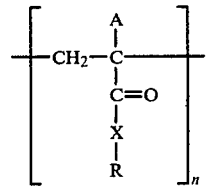

in which A is selected from hydrogen, lower alkyl of 1 to 5 carbon atoms, halide, nitro and nitrile, n is 10 to 10 million and

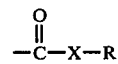

is selected from
(a) a group containing an amide linkage in which X is selected from a single bond and

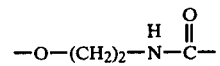

and R is a group obtained by removing an active hydrogen from an amino group of an amino containing compound selected from:
4-amino-6-tert=butyl-3-(methylthio)-as triazine-5(4H)one, 2-(ethylamine)-4(isopropylamino)-6-(methylthio-s-triazine)
3-amine-5-triazole
2-chloro-4-(ethylamino)-6-(isopropylamino)-s-triazine
3-amino-2,5-dichlorobenzoic acid
2-chloro-4-(cyclopropylamino)-6-(isopropylamino)-s-triazine
$N^4,N^4$-diethyl-a,a,a-trifluoro-3,5-dinitrotoluene-2,4-diamine
2-methoxy-4-ethylamino-6-sec-butylamino-s-triazine
4-amino-3,5-6-trichloropicolinic acid
2,4-bis(isopropylamino)-6-methoxy-s-triazine
2,4-bis(isopropylamino)-6-(methylthio)-s-triazine
2-chloro-4,6-bis(isopropylamino)-s-triazine
5-amino-4-chloro-2-phenyl-3(2H)-pyridazinone
2-chloro-4,6-bis(ethylamino)-s-triazine
2-chloro-4-ethylamino-6-tert-butylamino-s-triazine
2-methylthio-4-ethylamino-6-tert-butylamino-s-triazine
2-amino-3-chloro-1,4-naphthoquinone
2,4-dichloro-6(2-chloroanil-o)-1,3,5 triazine
3-amino-2,5-dichlorobenzoic acid;
(b) a group in which X is selected from a single bond, —NH—, —O—, —O—(CH$_2$)$_2$—NH-and —NH—(CH$_2$)$_2$—O— and R is a group obtained by removing a hydroxyl group from a carboxyl group of an acid selected from:
trichloroacetic acid
2,2-dichloropropionic acid (2,4-dichlorophenoxy)acetic acid 4-(2,4-dichlorophenoxy)butyric acid 2-(2,4-dichlorophenoxy)propionic acid (2,3,6-trichlorophenyl)acetic acid 2-methyl-4-chlorophenoxyacetic acid (2,4,5-trichlorophenoxy)acetic acid 2,3,6-trichlorobenzoic acid 2,3,5-triiodobenzoic acid 2,2,3-trichloropropionic acid 2-(3-chlorophenoxy)propionic acid 2-(4-chlorophenoxy)propionic acid 2,3,6-trichlorobenzoic acid and 3,5,6-trichloro-2-methoxybenzoic acid; and (c) a group in which X is a single bond and R is

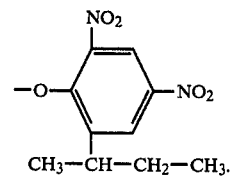

2. A pesticide polymer of claim 1 in which X is a single bond and R is 4-amino-6-tert-butyl-3-(methylthio)-as-triazine-5(4H)one.

3. A pesticide polymer of claim 1 in which X is

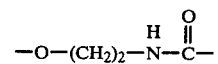

and R is 4-amino-6-tert-butyl-3-(methylthio)-as-triazine-5(4H)one.

4. A pesticide polymer of claim 1 in which R is trichloroacetic acid.

5. A pesticide polymer of claim 1 in which R is 2,2-dichloropropionic acid.

6. A pesticide polymer of claim 1 in which R is (2,4-dichlorophenoxy)acetic acid.

* * * * *